United States Patent
Laermer

(10) Patent No.: US 12,157,665 B2
(45) Date of Patent: Dec. 3, 2024

(54) PROCESS FOR PRODUCING A BASE OF AN ANALYSIS CELL FOR ANALYZING A BIOCHEMICAL MATERIAL, AND ANALYSIS CELL

(71) Applicant: Robert Bosch GmbH, Stuttgart (DE)

(72) Inventor: Franz Laermer, Weil der Stadt (DE)

(73) Assignee: Robert Bosch GmbH, Stuttgart (DE)

( * ) Notice: Subject to any disclaimer, the term of this patent is extended or adjusted under 35 U.S.C. 154(b) by 1060 days.

(21) Appl. No.: 17/052,868

(22) PCT Filed: May 2, 2019

(86) PCT No.: PCT/EP2019/061257
§ 371 (c)(1),
(2) Date: Nov. 4, 2020

(87) PCT Pub. No.: WO2019/215011
PCT Pub. Date: Nov. 14, 2019

(65) Prior Publication Data
US 2021/0238029 A1    Aug. 5, 2021

(30) Foreign Application Priority Data

May 8, 2018    (DE) ...................... 10 2018 207 101.2

(51) Int. Cl.
*B81C 1/00*    (2006.01)
*B01L 3/00*    (2006.01)
*G01N 33/48*    (2006.01)

(52) U.S. Cl.
CPC ...... *B81C 1/00047* (2013.01); *B81C 1/00349* (2013.01); *B01L 3/502707* (2013.01); *B01L 2300/161* (2013.01); *B81C 2201/0161* (2013.01); *B81C 2201/0174* (2013.01); *G01N 33/48* (2013.01)

(58) Field of Classification Search
None
See application file for complete search history.

(56) References Cited

U.S. PATENT DOCUMENTS

| | | | | |
|---|---|---|---|---|
| 9,834,445 | B2 * | 12/2017 | Kim | ...................... C01B 32/186 |
| 2013/0270188 | A1 * | 10/2013 | Karnik | ............... B01D 67/0062 216/36 |
| 2020/0062600 | A1 * | 2/2020 | Kidambi | ............. C23C 16/0227 |

OTHER PUBLICATIONS

Liu et al. A templating route to nanoporous chitosan materials, Carbohydrate Research, Dec. 2005, vol. 340, No. 18, 2816-8820.*
International Search Report corresponding to PCT Application No. PCT/EP2019/061257, mailed Jul. 25, 2019 (German and English language document) (4 pages).
Tang, Z. et al., "Fabrications, Applications and Challenges of Solid-state Nanopores: A Mini Review," Nanomaterials and Nanotechnology, 2016, vol. 6, No. 35, 1-12 (12 pages).
Liu, Y. et al., "A templating route to nanoporous chitosan materials," Carbohydrate Research, Dec. 2005, vol. 340, No. 18, 2816-2820 (5 pages).
Schneider, G. F. et al., "DNA Translocation through Graphene Nanopores," Nano Letters, Aug. 2010, vol. 10, No. 8, 3163-3167 (5 pages).
Rhee, M. et al., "Nanopore sequencing technology: nanopore preparations," Trends in Biotechnology, Mar. 2007, vol. 25, No. 4, 174-181 (8 pages).

* cited by examiner

*Primary Examiner* — David P Turocy
(74) *Attorney, Agent, or Firm* — Maginot, Moore & Beck LLP

(57) ABSTRACT

The disclosure relates to a process for producing a base of an analysis cell for analyzing a biochemical material. Here, carbon-rich precursor molecules and low-carbon precursor molecules are deposited on a substrate in a defined mixing ratio in order to form a precursor layer, wherein the low-carbon precursor molecules have a defined size and a hydrophobic end group. In a further step, the precursor layer is post-treated in a suitable manner in order to produce the base as a layer with at least one pore having a pore size dependent on the defined size and a pore count dependent on the defined mixing ratio.

12 Claims, 2 Drawing Sheets

PROCESS FOR PRODUCING A BASE OF AN ANALYSIS CELL FOR ANALYZING A BIOCHEMICAL MATERIAL, AND ANALYSIS CELL

This application is a 35 U.S.C. § 371 National Stage Application of PCT/EP2019/061257, filed on May 2, 2019, which claims the benefit of priority to Serial No. DE 10 2018 207 101.2, filed on May 8, 2018 in Germany, the disclosures of which are incorporated herein by reference in their entirety.

BACKGROUND

The disclosure proceeds from a method or a device according to the generic type of the embodiments.

The production of layers by atomic layer deposition, also called ALD for short, and of so-called self-assembled monolayers of precursor molecules, also called SAMs for short, is known. In this connection, the precursor molecules, also called precursors, dock, for example, with binding sites on a silicon or glass surface, it also being possible for the precursor molecules to crosslink with one another depending on the precursors. These processes are generally self-limiting, i.e., after deposition of a single monolayer and occupation of all available binding spaces of the surface, no further deposition with the same precursor takes place.

In the case of atomic layer deposition, what is achieved by at least one further precursor is that binding sites are formed again on a first deposited monolayer, meaning that a further monolayer can be subsequently deposited by means of the first precursor. This sequence of multiple precursors can be repeated as often as necessary until a desired layer thickness or number of monolayers has been deposited.

By contrast, in the case of self-assembled monolayers, only a single monolayer is formed on the surface and it is usually also intrinsically crosslinked. Once the entire surface is covered, including saturation of all available binding sites of the surface, there is no more deposition of precursor molecules on the surface. In most cases, this behavior is achieved by the precursor molecules docking in a selective manner on hydrophilic surfaces, generating themselves a hydrophobic surface while doing so, and thus automatically stopping further deposition because further precursor molecules are no longer able to dock on hydrophobic surfaces.

Such processes are well-known and well-controlled. Fully developed systems technology is available both for ALD layers and for self-assembled monolayers. In many cases, it is even possible to use the same system for both process types.

Self-assembled monolayers can also be deposited from the liquid phase with the aid of suitable solvents, for example hexane or heptane. However, owing to the higher purity of the precursor chemistry and to the better quality and reproducibility of the deposited layers, it is vapor deposition that has gained acceptance. This involves converting precursor molecules previously stored as liquid into vapor, for example by heating the precursor liquid. In a reaction chamber, the desired partial pressure of the precursor is set and contacted with the substrate. Methods with or without carrier gas (inert gas or noble gas such as, for example, N2 or Ar) are known.

It is further known that certain SAM coatings can be converted into graphene layers of qualitatively high value on wafers. To this end, the SAM coating after deposition on the substrate surface is, for example, covered with a 300 nm thick metal layer, for instance of nickel or copper, by vapor-coating and subsequently converted into graphene at a high temperature of 800° C. to 1000° C.

SUMMARY

Against this background, the approach presented here presents a method for producing a base of an analysis cell for analysis of a biochemical material and an analysis cell as set forth in the embodiments. Advantageous developments of and improvements to the device specified in the embodiments are possible by the measures stated in the disclosure.

The sequencing of a biochemical material, especially of DNA segments, can, for example, be carried out with the aid of a membrane composed of graphene or a nanometer-thick ALD layer that has, on the base of an array cell for a quantitative polymerase chain reaction, called qPCR for short, one nanopore or a few nanopores in each case. In this connection, the preparations for sequencing are, for example, achieved by a LATE-qPCR (LATE=linear after the exponential) in the array cells with a highly asymmetric number of forward and reverse primers characteristic of the respective array cell and specific for a characteristic DNA segment in each case, combined with a stop nucleotide characteristic of the respective array cell and of the type A*, T*, C* or G* in the manner of a Sanger sequencing method. When sequence-specific DNA fragments which are generated especially during the linear phase of the polymer chain reaction and which end with the stop nucleotide respectively characteristic of the array cell pass through the nanopores on the base of each qPCR array cell, it is possible to measure a change in an electric current flow and to determine as a result the passage time of the respective DNA fragment through the nanopore. It is thus possible to ascertain the respective length of the fragments passing through. The sum of all fragment lengths for respectively four array cells with the same primers and the stop nucleotides of the type A*, T*, C* or G* (respectively one type in each of the four array cells) yields the entire DNA sequence of the corresponding DNA segment defined by the primers.

The approach presented here makes it possible, then, to produce such nanopores in graphene layers or ALD layers in a cost-effective, simple and rapid manner by enrichment of low-carbon precursor molecules having hydrophobic termination in a particular mixture ratio with high-carbon precursor molecules on a substrate, the low-carbon precursor molecules contributing to forming gaps as nanopores in the layer which arises. A corresponding method for generating nanopores is universally suitable both for ALD layers and for the generation of graphene on the basis of self-assembled monolayers and is usable for both. The high-carbon precursor molecules and the low-carbon precursor molecules can differ in the number of carbon atoms comprised by the precursor molecules, it being possible for the high-carbon precursor molecules to have a greater number of carbon atoms.

A low-carbon precursor molecule, also called precursor, contributes little to no carbon at all for a subsequent conversion reaction into a graphene-type layer. A high-carbon precursor accordingly contributes much carbon.

Examples of low-carbon precursor molecules:
Cl3-Si—CH3 (only one carbon atom per precursor)
Cl3-Si—NH2, Cl3-Si—H, Cl2-Si—H2, SiCl4, . . . (no carbon atom at all per precursor)

Examples of high-carbon precursor molecules:
Cl3-Si—C6H5, Cl3-Si—(CnH2n+1), Cl2-Si—(CnH2n+1)-(CmH2m+1), . . . (n, m can be large numbers>10)

What is presented is a method for producing a base of an analysis cell for analysis of a biochemical material, the method comprising the following steps:

depositing high-carbon precursor molecules and low-carbon precursor molecules in a defined mixture ratio on a substrate in order to form a precursor layer, the low-carbon precursor molecules having a defined size and a hydrophobic termination; and aftertreating the precursor layer in order to produce the base as a layer having at least one pore with a pore size dependent on the defined size and with a pore number dependent on the defined mixture ratio.

An analysis cell can generally be understood to mean a cavern for prestorage of the biochemical material, for instance for carrying out a polymerase chain reaction. For example, the analysis cell can be designed as a qPCR array cell. A base can be understood to mean a wall segment having at least one opening through which the biochemical material can exit from the analysis cell, for instance for determining a length of individual fragments of the biochemical material or for sequencing the biochemical material. The biochemical material can, for example, be a sequence of nucleotides, for instance DNA, or the like. A precursor molecule can be understood to mean a molecule of a layer-forming starting material for deposition of a layer on a substrate. Such precursors can, for example, be organic trichlorosilanes, trimethoxysilanes or triethoxysilanes, for example octyltrichlorosilane, octadecyltrichlorosilane, decyltrichlorosilane, phenyltrichlorosilane, octyltrimethoxysilane, decyltrimethoxysilane, octadecyltrimethoxysilane, phenyltrimethoxysilane, octyltriethoxysilane, decyltriethoxysilane, octadecyltriethoxysilane or phenyltriethoxysilane. Trichlorosilanes are particularly suitable because, owing to their high chemical reactivity, they hydrolyze very rapidly and bond to hydroxyl groups of hydrophilic surfaces and also crosslink rapidly. However, methoxysilanes or ethoxysilanes can also be used. Phenylsilanes, especially trichlorophenylsilane, are particularly suitable for graphene generation because these precursor molecules already contain aromatic carbon rings corresponding to the later graphene structure. In the case of phenyltrichlorosilane, the starting material is in terms of its structure already similar to the target material, and this supports the subsequent thermal conversion of the aromatic carbon rings to graphene.

A substrate can, for example, be understood to mean a silicon or glass substrate. Depending on the embodiment, the precursor molecules can be deposited as vapor or in a liquid phase. A precursor layer can, for example, be understood to mean a self-assembled monolayer or a layer generated by atomic layer deposition, also called ALD layer. A low-carbon precursor molecule can be understood to mean a molecule having, in contrast to a high-carbon precursor molecule, a lack of carbon. For example, the low-carbon precursor molecules can be carbon-free or have only very few carbon atoms. The low-carbon precursor molecules can, for example, be based on a trichlorosilane chemistry and be hydrophobically terminated by a nitrogen or amide group. A pore can be understood to mean a nanopore having a diameter in the nanometer range.

Aftertreatment can, for example, be understood to mean a chemical, thermal or mechanical aftertreatment of the precursor layer. For example, this can involve at least one of the low-carbon precursor molecules forming a gap in the graphene layer that represents the pore. Alternatively, the low-carbon precursor molecules can be removed from the precursor layer at least in part during aftertreatment, for example by means of etching.

According to one embodiment, the precursor layer can be thermally converted into a graphene layer having the pore in the aftertreatment step. As a result, a rapid production of the base with high purity and high repeatability is made possible.

According to a further embodiment, the low-carbon precursor molecules can be removed at least in part from the precursor layer in the aftertreatment step in order to generate the pore. As a result of this embodiment too, a rapid production of the base with high purity and high repeatability is made possible, especially when the precursor layer is formed by means of atomic layer deposition.

Furthermore, it is advantageous when the low-carbon precursor molecules are deposited in the form of nanoparticles in the deposition step. Nanoparticles can be understood to mean prefabricated particles having a size in the nanometer range, for example silicon-based nanoparticles, also called silica beads, or similarly suitable, commercially available nanoparticles. As a result, a particularly cost-effective production of the base is made possible.

The method can comprise a step of forming molecule clusters of at least two low-carbon precursor molecules in a liquid phase. In this connection, the molecule clusters can be deposited on the substrate in the deposition step in order to form the precursor layer. As a result, a diameter of the pore to be generated in the base can be set in a very precise and controlled manner with comparatively little effort.

In this connection, the molecule clusters can be formed by polycondensation and/or polymerization in the formation step. As a result, the molecule clusters can be formed in a particularly simple and rapid manner.

According to a further embodiment, the high-carbon precursor molecules and the low-carbon precursor molecules can be deposited in the deposition step in a mixture ratio defined in such a way that the base is produced as a layer having not more than three pores in the aftertreatment step. As a result, it is possible to prevent the base from being produced with an excessively large number of pores.

According to a further embodiment, a self-assembled monolayer enriched with the low-carbon precursor molecules can be formed as the precursor layer in the deposition step. As a result of this embodiment, it is possible to ensure that the base is produced as a layer which is low in defects as far as possible and has a uniform structure.

Furthermore, the substrate can be pretreated in a pretreatment step in order to generate a hydrophobic surface of the substrate. The hydrophobic surface can be exposed to water vapor in an exposure step in order to generate a surface statistically enriched with OH groups. Lastly, the low-carbon precursor molecules can be deposited in a statistical manner on the surface statistically enriched with OH groups in the deposition step in order to subsequently generate a hydrophilic surface having hydrophobic islands of the low-carbon precursor molecules. In addition, the high-carbon precursor molecules can be deposited on the subsequently hydrophilically rendered surface in order to form the precursor layer. As a result, it is possible to produce the base with particularly high purity and quality.

A "hydrophobic pretreatment of the surface" can therefore be carried out. In this connection, the surface can be made hydrophobic over the entire surface, for example using hydrofluoric acid. Thereafter, the surface which is hydrophobic over the entire surface can be made hydrophilic in a statistical manner. This can be understood to mean that the surface is not exactly made uniformly hydrophilic, but that a few hydrophilic islands are generated in a statistical uniform distribution across the surface as a result of action of water vapor. In this connection, what is particularly conducive to the statistical distribution of the hydrophilic islands generated by water vapor is the fact that this hydrophilization of silicon oxide surfaces starts after a hydrofluoric-acid treatment from statistically distributed fluorine atoms on the surface compared to a generally dominating hydrogen termination, and then slowly spreads across the silicon oxide surface proceeding from these "seeds" until the hydrophilization process is when the stopped desired size of the hydrophilic islands is reached. The arrangement of the islands can therefore be random in the context of the process parameters. In what follows, these statistically uniformly distributed hydrophilic islands can then be made low-carbon by coating with low-carbon precursors, which are fixed there. Thereafter, the rest of the surface can be made completely hydrophilic, for example by action of water vapor. Thereafter, the rest of the surface can receive a high-carbon coating by means of high-carbon precursors.

According to a further embodiment, low-carbon the precursor molecules can be deposited at a temperature of 5° C. to 30° C. in the deposition step. Additionally or alternatively, the high-carbon precursor molecules can be deposited at a temperature of greater than 40° C. in the deposition step. As a result, a comparatively simple temperature-controlled production of the base is made possible.

For example, the high-carbon precursor molecules can be deposited in the deposition step after deposition of the low-carbon precursor molecules after expiration of a cross-linking time, during which the deposited low-carbon precursor molecules are crosslinked with one another and/or with the substrate at a crosslinking temperature. As a result, the high-carbon precursor molecules can be deposited on a stably crosslinked structure.

Depending on the embodiment, the high-carbon precursor molecules and/or the low-carbon precursor molecules can be deposited in the deposition step by means of atomic layer deposition, vapor deposition, liquid-phase deposition or by means of a plurality of the stated coating methods. As a result, an efficient, cost-effective production of the base is made possible.

According to a further exemplary embodiment, low-carbon precursor molecules which are hydrophobically terminated by at least one nitrogen group and/or at least one amide group can be deposited in the deposition step. As a result, a simple synthesis of the low-carbon precursor molecules is made possible.

Lastly, the approach presented here provides an analysis cell for analysis of a biochemical material, comprising a base which was produced as a layer having at least one pore in a method as per any of the preceding embodiments.

BRIEF DESCRIPTION OF THE DRAWINGS

Exemplary embodiments of the disclosure are depicted in the drawings and more particularly elucidated in the following description, where.

DETAILED DESCRIPTION

In the following description of favorable exemplary embodiments of the present disclosure, identical or similar reference signs are used for the elements which are depicted in the various figures and act in a similar manner, in order to dispense with a repeated description of said elements.

In what follows, the method is described in detail for the generation of nanopores in graphene by way of example. However, it is understandable to a person skilled in the art that the method also works in the case of ALD processes and can be applied thereto without restriction.

Figure 1:
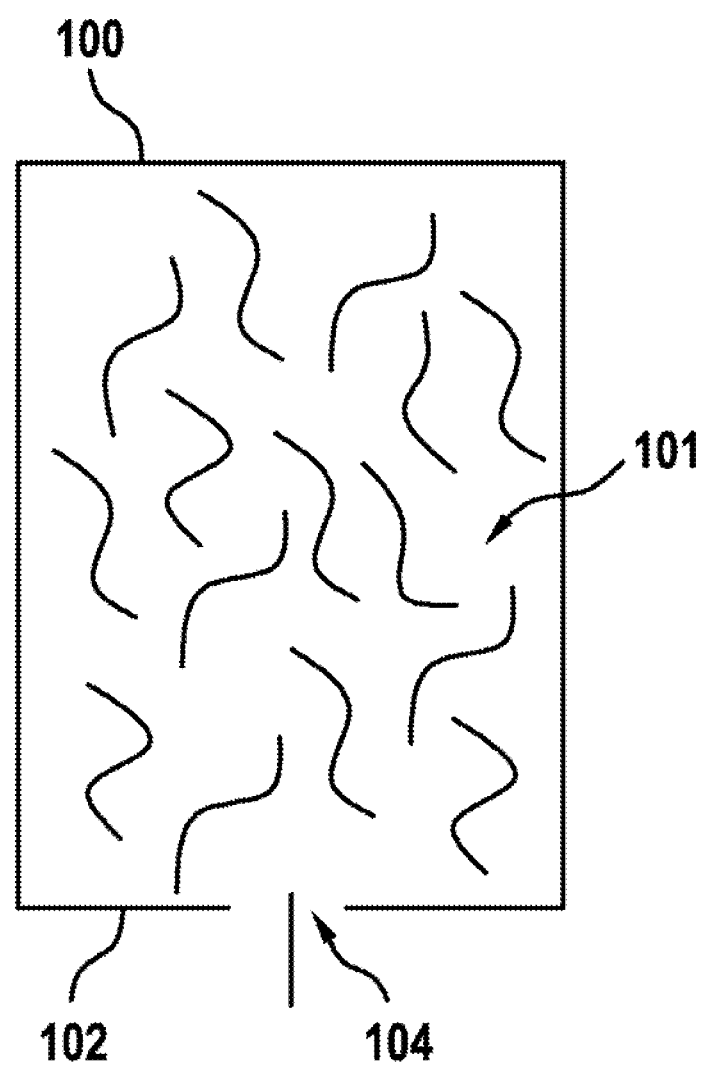
FIG. 1 shows a schematic representation of an analysis cell as per one exemplary embodiment.

FIG. 1 shows a schematic representation of an analysis cell 100 as per one exemplary embodiment. The analysis cell 100 for analysis of a biochemical material 101, for example an array cell for carrying out a quantitative polymerase chain reaction, is realized as a cavern having a base 102. The base 102 has a pore 104 through which the biochemical material 101, for example for sequencing or determination of fragment length, can exit from the analysis cell 100. The pore 104 is designed as a nanopore. According to this exemplary embodiment, the base 102 is produced as a graphene layer, the pore 104 having been generated upon thermal conversion of an appropriate precursor layer into the graphene layer, for instance of a self-assembled monolayer, with the aid of low-carbon precursor molecules having hydrophobic termination. In this connection, the precursor layer, which is predominantly composed of high-carbon precursor molecules, was enriched with the low-carbon precursor molecules in a suitable coating method such as, for example, atomic layer deposition, vapor deposition or liquid-phase deposition. In this connection, the low-carbon precursor molecules were admixed with the precursor layer in a defined mixture ratio, through which a mean number of pores 104 in the base 102 is defined, for example a mean number of not more than three pores 104. Furthermore, the low-carbon precursor molecules have a defined size, through which a size of the pore 104 is defined in turn. As a result of an appropriate aftertreatment of the precursor layer, in this case by heating of the precursor layer, what forms at the incorporation site of at least one of the low-carbon precursor molecules is a gap in the carbon structure of the graphene layer which arises upon heating. Said gap represents the pore 104.

The basic concept of the approach described here is the incorporation, in the self-assembled monolayer serving as starting material for the generation of the graphene layer on a surface appropriate substrate, of molecules or molecule clusters of a second precursor type in a statistical distribution, which molecules or molecule clusters contribute no carbon or only very little carbon for graphene formation. If such a precursor molecule of sufficient largeness is incorporated together with other precursor molecules, for instance phenyltrichlorosilane, in the monolayer, what arises in the subsequent thermal treatment and conversion of the monolayer into the graphene layer at the site of the carbon-free or low-carbon molecule or molecule cluster is a gap which leads to the formation there of a nanopore in the graphene layer. Besides a sufficient size, said carbon-free precursor molecule should also have a hydrophobic termination, for example due to nitrogen (N) or amide (NH$_2$) groups. The nitrogen atoms or amide groups also generate a hydrophobic surface at the location of the specific precursor molecules. At the sites where these precursor molecules are incorporated, the hydrophobic termination also achieves a self-stopping property, i.e., there is also no more deposition of further high-carbon precursor molecules there or thereabove.

Figure 2:
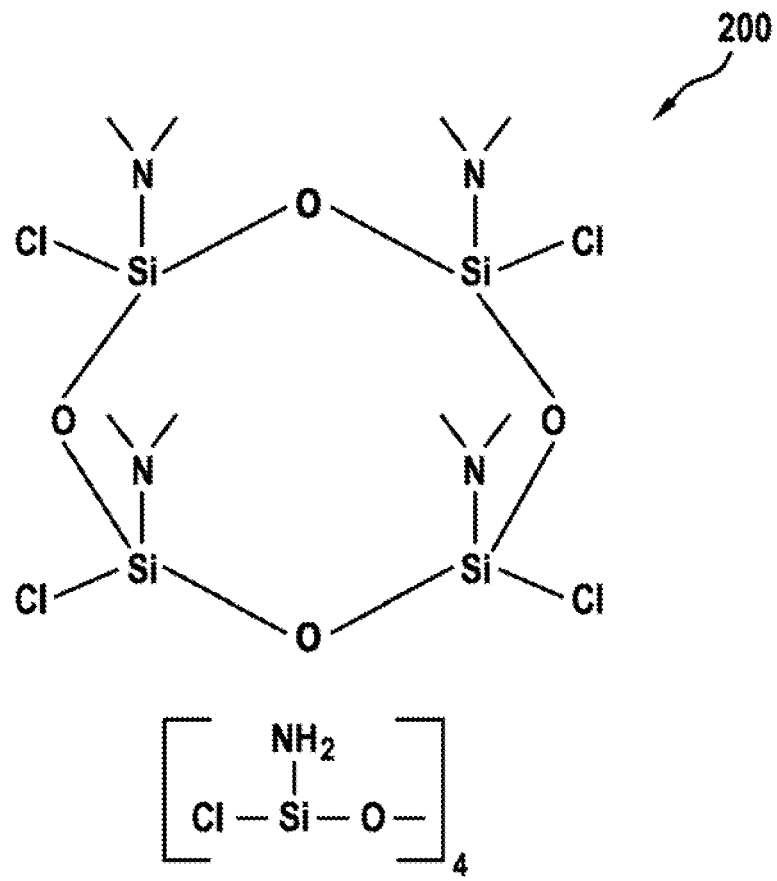
FIG. 2 shows a schematic representation of a structure of a low-carbon precursor molecule for use in a method as per one exemplary embodiment.

FIG. 2 shows a schematic representation of a structure 200 of a carbon-free precursor molecule for use in a method as per one exemplary embodiment. A suitable is, for based a example, precursor molecule on trichlorosilane chemistry, as shown in FIG. 2 by way of example. The basic structure of the precursor molecule [Cl—Si(NH$_2$)—O—]$_4$ already corresponds to a base cell of the type [—O—Si(NH$_2$)—O—]$_4$, which is formed in a periodic manner on the substrate during deposition. Alternatively, it is also possible to use other molecules which insert into the monolayer, for example of phenyltrichlorosilane, in a statistical manner and ensure a hydrophobic termination of the surface. It is also possible to use carbon-free or at least low-carbon terminations different from nitrogen, for instance a single carbon atom per silicon atom. Hereinafter, the term "carbon-free" is equated with a lack of carbon, this also including the term "low-carbon".

The size of an "imperfection" or the nanopore in the later generated graphene layer is determined by the size of the specific carbon-free precursor molecule, with, according to one exemplary embodiment, multiple elementary cells of a basic structure being put together during synthesis for molecule enlargement, for example as a molecule of the form [Cl—Si(NH$_2$)—O—]$_{4n}$ where n=1, 2, 3, . . . .

The use of a chlorosilane chemistry, as cited here as an example, can correspondingly also be applied to a methoxysilane chemistry or ethoxysilane chemistry by replacement of Cl with OCH$_3$ or OC$_2$H$_5$.

During the thermally induced conversion of the monolayer, the carbon achieves a certain mobility, i.e., the carbon atoms can move relatively freely on the substrate surface between substrate and metal topside underside and reorganize to form a graphene layer. Despite this mobility, the available carbon is, however, not able to cover relatively large carbon-free molecule clusters, with the result that what forms there is a nanopore, the size or diameter of which correlates with the size of the specific carbon-free precursor molecule—with the extent of the local lack of carbon.

The number of nanopores correlates in turn with the relative proportion of the carbon-free precursor molecules in relation to the high-carbon precursor molecules, for example of the type phenyltrichlorosilane. The more carbon-free precursor molecules that are admixed, the higher the density of the nanopores thereby generated in the graphene layer. Advantageously, the density of the nanopores is set such that there are 1 to 3 nanopores, especially 1 to 2 nanopores, on average per surface area of a cavern base of the analysis cell. Each base of an analysis cell should therefore contain at least one and not more than two nanopores. It is also possible to create a larger number of nanopores per analysis cell. However, nonspecific passage events can be expected in this case when there is simultaneous movement of DNA fragments in multiple nanopores. This situation can be identified beyond doubt from the current flow profile and the data sets affected can be eliminated for the purpose of correction. In such a case, the length information of the DNA fragments just passing through the pores is, however, lost each time. Nanopores outside array cells, i.e., nanopores which do not come upon a cavern base, have no significance and no function. They do not interfere with the use of the nanopores for determining the length of DNA fragments which pass from the qPCR cells through the nanopores on the cavern base. Depending on the exemplary embodiment, the graphene layer having the nanopores is either copied, i.e., transferred, from a support substrate onto an array cell wafer or the deposition is carried out directly on the array cell wafer using an additional sacrificial layer technology or a stop layer for a DRIE process (DRIE=deep reactive ion etching), for example in the form of a SiO$_2$ stop layer.

The deposition of the monolayer is, for example, carried out from a liquid phase using a solvent such as hexane or heptane or, this being particularly advantageous, from a vapor or gas phase of the precursor molecules. In the case of a liquid-phase deposition, the appropriate ratio of phenyltrichlorosilane (or another suitable SAM precursor) and the carbon-free chlorosilane is simply admixed with the solvent. In the case of a vapor deposition, the appropriate ratio is set via the partial pressures of the two precursor molecules, which usually vary in the hectopascal range. The carbon-free precursor molecules are, for the reasons described, distinctly larger and heavier than, for example, phenyltrichlorosilane and therefore also have a correspondingly lower vapor pressure at a given temperature. However, this does not have a detrimental effect, since they are also only required in a distinctly lower concentration or under a distinctly lower partial pressure. The partial pressures are set by appropriately choosing the respective precursor temperature and hence the respective vapor pressure or by using mass flow controllers to supply the two molecule types. Alternatively, appropriate gas volumes are transferred one-time only or periodically from appropriately dimensioned gas storage tanks into the actual reaction chamber.

In the case of an atomic layer deposition, the nanopores are generated by using not only a majority precursor, but also further minority precursor molecules which, for example, make a further deposition impossible at the location and site where they were incorporated, i.e., when switching to the second majority precursor, no new binding sites are established at the integration sites of the minority precursor molecules. After completion of the ALD process, the minority precursor molecules are, for example, selectively removed, for example selectively etched, thus yielding a nanopore at the affected site.

It is therefore possible to produce graphene layers or ALD layers having a uniform distribution of nanopores having a predetermined size and density in a simple, rapid and cost-effective method. Apart from the use of specific precursor molecules, there is no need for special machines and equipment which are not available in any case in a semiconductor or MEMS factory. This means that it is possible to use the method in structures which are widely established industrially.

In one variant, the growth of the monolayer is, for example, achieved in an insular manner at low deposition temperatures of less than 20° C., especially at 10° C. In what follows, such growth is described using the example of a vapor deposition.

Insular growth is based on the occurrence at low temperatures of a spontaneous seeding of the substrate surface with a statistical distribution due to SAM precursor molecules which, though mobile on the surface for a certain time, especially at higher temperatures of greater than 40° C., are frozen so to speak at their docking location because of the low temperatures and grow laterally as time progresses. By contrast, what occurs at higher temperatures of, for example, 70° C. is a uniform coverage with SAM precursor molecules because of the high mobility of the precursors on the substrate surface.

The density of the islands on the substrate surface that are formed at a low temperature is dependent on the reactivity of the precursor system, on the partial pressure of the precursor molecules, on the deposition time, on the nature of the surface itself and especially on the density of the available hydrophilic seeding sites on the surface. During insular growth, further precursor molecules dock with the seeds formed once on the surface and crosslink therewith transversely by a condensation reaction of the silanol groups.

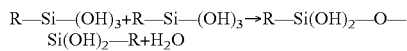
$$R\text{—}Si\text{—}(OH)_2\text{—}R+H_2O$$

In this way, more and more precursor molecules construct an increasingly larger molecule cluster on the surface. After a certain time, which can be several hours at low temperatures of 10° C. for example, the crosslinking of the molecules both with one another and toward the substrate becomes irreversible, i.e., chemical bonds of the form-Si—O—Si— are constructed both between the molecules and toward the binding sites of the substrate.

The density of the seeding sites is controlled as follows. If a silicon or glass substrate or a $SiO_2$ surface is etched with dilute hydrofluoric acid HF, the hydrophilic OH groups on the surface disappear and are replaced by a hydrophobic termination due to H and F atoms. This surface does not have long-term stability and is therefore slowly changed back into an OH-terminated surface, for example by action of water vapor. This process takes place over the time scale in a statistical manner with a uniform distribution over the surface. SAM precursor molecules as seeds from which further insular growth proceeds subsequently dock with the reformed OH groups.

One exemplary embodiment of the approach presented here consists, then, in first growing such islands using carbon-free or at least low-carbon precursors of a first type in a first step. This is, for example, possible with very simple precursor molecules, such as, for instance, $HSiCl_3$, $H_3CSiCl_3$, $H_3CSi(CH_3O)_3$, $NH_2Si(CH_3O)_3$ or $NH_2Si(C_2H_5O)_3$. There is a multiplicity of such small silanes which can grow in accordance with the described mechanism and can provide a hydrophobic surface termination without carbon atoms or with only a few carbon atoms. To this end, the wafer substrate is, as described above, provided with a hydrophobic surface over the entire surface by pretreatment with dilute hydrofluoric acid HF. Thereafter, the wafer substrate is transferred into an SAM coating machine and exposed to a pretreatment with introduced water vapor. During this, what is generated over time in a controlled manner is a growing density of hydrophilic OH groups with a uniform statistical distribution over the surface. What are thus formed are a few hydrophilic islands in a statistical uniform distribution over the surface. Thereafter, the SAM coating is started with the carbon-free precursor molecules of the first type at a low temperature of 10° C. to 20° C., this leading to formation of carbon-free or at least low-carbon molecule clusters, the islands, on the surface that grow laterally over time.

Once enough islands of the desired size have been formed, the first step of the coating process is interrupted and the wafer substrate is stored at a low temperature, for example for 24 hours under an atmosphere. What occurs during this time is the irreversible crosslinking of the precursor molecules with one another and with the substrate surface as a result of formation of chemical bonds. In addition, all hydrophobic groups (H or F) of the substrate surface are converted to hydrophilic OH groups over this time span owing to the air humidity or owing to water vapor supplied in a controlled manner. The result is a hydrophilic wafer having hydrophobic carbon-free molecule clusters which are present with a uniform statistical distribution and in an immobilized state on the substrate surface.

In the next step, the wafer substrate is transferred back into the SAM coating machine and conditioned again with water vapor. At an elevated temperature of greater than 40° C., for example at 70° C., what then takes place is a second SAM coating step with suitable high-carbon a second type, which are precursor molecules of subsequently converted into a graphene layer by high-temperature treatment under a metal layer, for instance of copper or nickel. For this purpose, use is made of, for example, octyltrichlorosilane, decyltrichlorosilane, phenyltrichlorosilane or corresponding alkoxysilanes. It is essential that this layer only grows on hydrophilic parts of the surface where no carbon-free molecule clusters or carbon-free islands are situated, since what is present there is a hydrophobic surface, over which no further precursor can molecules grow. Therefore, a substrate surface having a precursor species suitable for graphene generation, interrupted by carbon-free molecule clusters or islands which define the later nanopores, is generated.

As already described, what can be incorporated in the monolayer serving as starting material for the generation of the graphene layer on the substrate surface molecule clusters of a differing precursor type in a statistical distribution, the molecule clusters contributing no carbon or only very little carbon for graphene formation. The formation of these relatively large nano-molecule clusters is, for example, achieved in a self-assembled manner from the reaction of small, simply constructed and readily available low-carbon or carbon-free silanes, preferably in a liquid phase, before there is contact with the substrate surface to be coated and statistical deposition of the formed molecule clusters on the substrate surface. If such a sufficiently large precursor molecule cluster is present in the monolayer on the substrate surface together with the, for example, subsequently applied phenyltrichlorosilane precursor molecules, what arises in the subsequent thermal treatment and conversion of the monolayer into the graphene layer at the site of the carbon-free molecule cluster is a gap, which leads to the formation there of a nanopore in the graphene layer. Besides a sufficient size, said carbon-free precursor molecule cluster also has a hydrophobic termination, for example due to nitrogen (N), amide ($NH_2$), methyl, carbon or hydrogen groups. Said groups also generate a hydrophobic surface at the location of the specific precursor molecule cluster, the result being that a self-stopping effect occurs in a second deposition step of the coating process, i.e., there is also no more deposition of further SAM precursor molecules there or thereabove.

According to a further exemplary embodiment, a liquid-phase deposition is used for a first deposition of carbon-free or low-carbon precursor molecule clusters on a substrate surface. In a liquid phase, reactions of the carbon-free or low-carbon precursor molecules to form molecule clusters can be controlled better than in vapor. In this connection, the agglomeration of dissolved carbon-free or low-carbon precursor molecules with a reaction partner to form nanoparticles or nano-molecule clusters and the subsequent deposition thereof on a substrate surface is utilized in a controlled manner in order to define nanopores in a graphene layer that is later thermally generated. The goal is to avoid an explicit synthesis of large silanes. On the contrary, said nano-molecule clusters are also to be formed in a self-assembled process from small, simply constructed and readily available silanes and to be subsequently deposited on the substrate surface in a statistical distribution. This is, for example, initiated by addition of a small amount of water to the solution of the precursor molecules of the first type in a suitable solvent such as hexane, heptane or chlorinated (hydro) carbon.

By contrast, the actual SAM coating of the entire substrate surface, with the exception of the carbon-free or low-carbon molecule clusters already present, with a high-carbon silane precursor preferably occurs in a second deposition by means of vapor deposition in order to obtain SAM layers which are low in defects as far as possible and are well-defined and which can subsequently provide a graphene layer low in defects.

The initiation reaction of the low silanes for formation of nano-molecule clusters in solution is a hydrolysis with the water likewise added in a small amount:

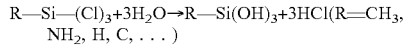
$$R-Si-(Cl)_3+3H_2O \rightarrow R-Si(OH)_3+3HCl (R=CH_3, NH_2, H, C, \ldots)$$

Depending on the available water content, the hydrolysis also occurs only in part, i.e., in the latter case, both OH and Cl groups remain on the molecule.

As a result, a certain amount of trichlorosilane, as used in the chosen example, is converted to hydroxysilane, i.e., condensation seeds are formed in the liquid phase depending on the amount of dissolved trichlorosilane and especially depending on the amount of added water. The concentration of the condensation seeds depends on the amount of the reaction partners, especially on the amount of added water. What takes place subsequently and over the reaction time is a polycondensation of the silanol molecules to form silanol molecule nanoclusters. In this connection, both silanols and (unreacted) chlorosilanes can additionally attach to a molecule cluster and enlarge it. Lastly, the size to be achieved by the nano-molecule clusters is controlled via the time parameter. A few examples of polycondensation reactions are listed below.

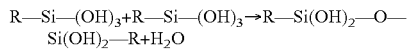
$$R-Si-(OH)_3+R-Si-(OH)_3 \rightarrow R-Si(OH)_2-O-Si(OH)_2-R+H_2O$$

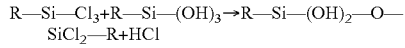
$$R-Si-Cl_3+R-Si-(OH)_3 \rightarrow R-Si-(OH)_2-O-SiCl_2-R+HCl$$

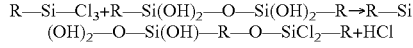
$$R-Si-Cl_3+R-Si(OH)_2-O-Si(OH)_2-R \rightarrow R-Si(OH)_2-O-Si(OH)-R-O-SiCl_2-R+HCl$$

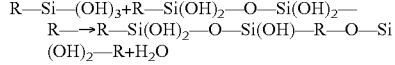
$$R-Si-(OH)_3+R-Si(OH)_2-O-Si(OH)_2-R \rightarrow R-Si(OH)_2-O-Si(OH)-R-O-Si(OH)_2-R+H_2O$$

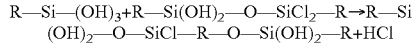
$$R-Si-(OH)_3+R-Si(OH)_2-O-SiCl_2-R \rightarrow R-Si(OH)_2-O-SiCl-R-O-Si(OH)_2-R+HCl$$

Thus, there are either condensation reactions of hydrolyzed or partially hydrolyzed molecules (silanols) on a molecule cluster under construction with release of water, which can hydrolyze further tricholorsilanes in immediate proximity the molecule cluster under construction, or else a direct attachment of trichlorosilanes to a molecule cluster under construction. Density and size of molecule clusters are therefore decoupled to a certain extent and controllable independently of one another. When the size of the nano-molecule clusters in the liquid phase corresponds to the desired value range, the substrate to be coated is contacted with the liquid phase and the nano-molecule clusters dock, owing to their OH bonds or their Cl groups, with the substrate surface, with hydrophilic binding sites (OH groups on the substrate surface) or so-called seeding sites being particularly attractive for this purpose. As further a supporting parameter for influencing the density of the nano-molecule clusters which are to bind to the substrate surface, it is possible to modify the density of such seeding sites on the substrate surface. If a silicon substrate or a glass substrate or a $SiO_2$ surface is etched with dilute hydrofluoric acid HF, the hydrophilic OH groups on the surface disappear and are replaced by a hydrophobic termination due to H and F atoms. This surface does not have long-term stability and is slowly changed back into an OH-terminated surface, for example by action of water vapor or in a humid atmosphere. This process takes place over the time scale in a statistical manner with a uniform distribution over the surface and in a very slow manner and is thus easily controllable over time. The nano-molecule clusters can subsequently dock particularly effectively with the OH reformed groups, this representing a further influencing parameter besides the density of the nano-molecule clusters in the liquid phase.

To this end, the wafer substrate is, as described above, provided with a hydrophobic surface over the entire surface by pretreatment with dilute hydrofluoric acid HF. Thereafter, the wafer substrate is exposed to a water vapor-containing atmosphere for a certain time. During this, what is generated over time in a controlled manner is a growing density of hydrophilic OH groups with a uniform statistical distribution over the surface. The wafer substrate is then introduced into the liquid phase at a preferably low temperature of 10° C. to 20° C., in which the desired density and size of silane nano-molecule clusters was generated beforehand from a silane precursor of the first type and an appropriate amount of water. While the substrate wafer is exposed to the liquid phase, what take place are docking of nano-molecule clusters with the hydroxyl groups of the substrate surface and formation of low-carbon islands, which are less mobile owing to the low temperature and ultimately completely immobilize on the substrate surface.

Afterwards, the wafer substrate is stored at a preferably low temperature of, for example, 10° C. to 20° C., for example for 24 hours under an atmosphere. What occurs during this time is the irreversible crosslinking of the nano-molecule clusters with the substrate surface as a result of formation of chemical bonds. In addition, all hydrophobic groups (H or F) of the substrate surface are converted to hydrophilic OH groups and all chlorine atoms are removed from the layer by hydrolysis over this time span owing to the air humidity or owing to water vapor supplied in a controlled manner. The result is a hydrophilic wafer having hydrophobic carbon-free molecule clusters which are present with a uniform statistical distribution and in an immobilized state on the substrate surface.

In the next step, the wafer substrate is transferred into a vapor SAM coating machine. At an elevated temperature of greater than 40° C., for example at 70° C., what then takes place is a second SAM coating step with suitable high-carbon precursor molecules of a second type, which are subsequently converted into the graphene layer by high-temperature treatment under a metal layer, for instance of copper or nickel, that is also to be subsequently applied. For this purpose, use is made of, for example, octyltrichlorosilane, decyltrichlorosilane, octadecyltrichlorosilane, phenyltrichlorosilane or corresponding alkoxysilanes. It is essential that this layer only grows on hydrophilic parts of the surface where no carbon-free molecule clusters are situated, since what is present there is a hydrophobic surface, over which no further precursor molecules can grow. The result is a substrate surface having a precursor species suitable for graphene generation, interrupted by carbon-free molecule clusters which define the later nanopores.

The number of nanopores correlates in turn with the number of carbon-free or low-carbon precursor molecule clusters. The more carbon-free precursor molecule clusters that are present on the surface, the higher the density of the nanopores thereby generated in the graphene layer. The larger the carbon-free precursor molecule clusters that are polycondensed or polymerized before deposition, the larger the respective nanopore.

Alternatively, the base is generated using nanoparticles which are commercially available and are cost-effectively industrially manufactured. As a result, it is possible to achieve simple processing and good and simple process control.

In this connection, the nanoparticles are used for the first deposition on the substrate surface. It is particularly advantageous that the number, density and size thereof can be determined in a simple manner and that the uncertainty f an in situ production is eliminated from the overall process. The process is started under well-defined and well-controlled conditions, as regards size and number of the applied nanoparticles.

Numerous suppliers offer a large selection of industrially produced nanoparticles in different sizes from about 10 nm in diameter and of a very wide variety of different materials that can be purchased in large quantities at reasonable prices. Although a multiplicity of materials is suitable in principle for the proposed method, the use of silicate nanoparticles composed of $SiO_2$ appears to be particularly advantageous. Numerous alternatives exist with respect to the size and the quality of such nanoparticles, right up to porous nanoparticles which can be loaded with further substances.

The substrate surface to be coated is advantageously first hydrophilized according to one of the known methods.

Afterwards, a solution containing the desired number of nanoparticles as a suspension, i.e., having a certain concentration of such nanoparticles in a dispersed state, is applied to the surface. These are, for example, the abovementioned silica beads. The solvent or carrier used for the bead suspension is water or an organic solvent, for example an alcohol, hexane, heptane or a chlorinated (hydro) carbon. By evaporation of the solvent, the predetermined number of nanoparticles, preferably of silicate nanoparticles, remains on the substrate surface. Alternatively, the bead dispersion is spun on, for example using a wafer spinner, for application and drying. The latter is, for example, advantageous when the substrates are silicon wafers. In the case of the spinning method, the density of the nanoparticles on the surface must be ascertained experimentally and depending on spinning speed and spinning speed ramp, since some of the solution containing the nanoparticles is lost during spinning, i.e., is spun way even before drying.

After drying of the substrate surface, the nanoparticles are bound by adhesion forces to the surface and are immobilized there. In the case of use of silica beads, there are van der Waals forces via the hydroxyl groups, though first chemical bonds between substrate surface and nanoparticles can also form by condensation reactions. The nanoparticles thus mask parts of the substrate surface on which they are immobilized.

During the SAM coating process, the nanoparticles sitting on the substrate surface act as masking, i.e., where they sit, coating of the substrate surface does not take place. Since approximately spherical nanoparticles are concerned, the masked or covered surface area is smaller than the diameter of a nanoparticle. In this respect, a diameter of 10 to 20 nm for silicate nanoparticles is definitely suitable for masking for generation of imperfections intended to lead to nanopores in graphene.

At the same time, it is irrelevant whether the nanoparticles sitting on the substrate surface are themselves coated with the monolayer or not. Silicate nanoparticles can, via their hydroxyl groups, actually be coated with SAM precursors. In the case of other materials, it is possible that no coating occurs.

After completion of the SAM coating process, the monolayer is present in a chemically stably bound form on the substrate surface. The chemical bonds to the substrate surface via Si—O—Si bonds and the crosslinking of the silanol groups with one another are irreversible.

In this state, the nanoparticles are removed from the substrate surface. In this connection, mechanical forces are preferably used, for example an ultrasonic cleaning of the wafer in an ultrasonic bath below the cavitation threshold or a megasonic cleaning of the wafer, i.e., an ultrasonic cleaning with frequencies in the megahertz range, which generates no cavitation in a megasonic bath and is particularly highly suited for removing tiniest particles or nanoparticles from substrate surfaces. Also possible is a blow-off of the wafer using pressurized air or other gases, a gentle blow-off using frozen carbon dioxide or frozen argon (e.g., frozen by Joule-Thomson expansion from a nozzle) or a rinse-off using a water jet or other liquids that are moved. During this, the nanoparticles are removed from the substrate surface, while the monolayer remains intact owing to its stable chemical bonds to the substrate surface. To protect the monolayer from damage, severe actions such as, for instance, cavitation effects should be absolutely avoided.

Apart from the use of commercially available and industrially produced nanoparticles composed of materials such as, for example, $SiO_2$, which is fundamentally semiconductor-compatible, there is no need for special machines and equipment which are not available in any case in a semiconductor or MEMS factory. This means that it is possible to use the method in structures which are widely established industrially.

Figure 3:
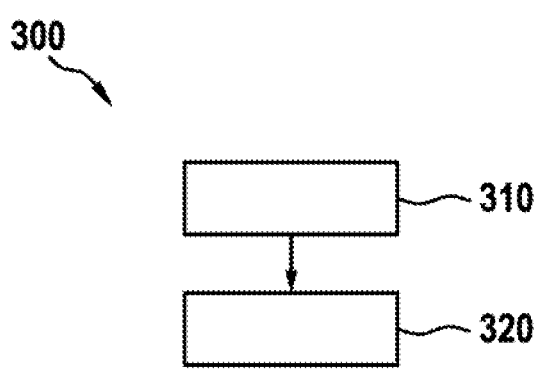
FIG. 3 shows a flow chart of a method as per one exemplary embodiment.

FIG. 3 shows a flow chart of a method 300 as per one exemplary embodiment. The method 300 for producing a base of an analysis cell, for instance the analysis cell described on the basis of FIG. 1, comprises a step 310 in which the deposition of the high-carbon and low-carbon precursor molecules on a suitable substrate takes place. A precursor layer is formed in this connection, for example a self-assembled monolayer as starting layer for producing a graphene layer, or an ALD layer. In a further step 320, the aftertreatment of the precursor layer is carried out. In this connection, the precursor layer is converted into a layer which acts as the base and has at least one pore, the pore size being defined by the defined size of the low-carbon precursor molecules and the pore number being defined by the defined mixture ratio in which the high-carbon and low-carbon precursor molecules are deposited on the substrate.

If an exemplary embodiment comprises an "and/or" link between a first feature and a second feature, this is to be interpreted as meaning that the exemplary embodiment comprises both the first feature and the second feature according to one embodiment and either only the first feature or only the second feature according to a further embodiment.

The invention claimed is:

1. A method for producing a base of an analysis cell for analysis of a biochemical material, the method comprising:
depositing high-carbon precursor silane molecules, having six (6) or more carbon atoms, and low-carbon precursor silane molecules, having one (1) or zero (0) carbon atoms, in a defined mixture ratio on a substrate thereby forming a precursor layer, the low-carbon precursor molecules having a defined size and a hydrophobic termination;

aftertreating the precursor layer thereby producing the base as a layer having at least one pore with a pore size dependent on the defined size and with a pore number dependent on the defined mixture ratio; and wherein aftertreating further comprises thermally converting the precursor layer into a graphene layer having the at least one pore.

2. The method as claimed in claim 1, wherein aftertreating further comprises:
removing the low-carbon precursor molecules at least in part from the precursor layer in thereby generating the at least one pore.

3. The method as claimed in claim 1, wherein depositing further comprises:
depositing the low-carbon precursor molecules in the form of nanoparticles.

4. The method as claimed in claim 1, further comprising:
forming molecule clusters of at least two low-carbon precursor molecules in a liquid phase, wherein depositing further comprises:
depositing the molecule clusters on the substrate thereby forming the precursor layer.

5. The method as claimed in claim 4, wherein forming further comprises:
forming the molecule clusters by one or more of polycondensation and polymerization.

6. The method as claimed in claim 1, wherein depositing further comprises:
depositing the high-carbon precursor molecules and the low-carbon precursor molecules in a mixture ratio defined such that the base is produced as a layer having not more than three pores in the aftertreating.

7. The method as claimed in claim 1, wherein depositing further comprises:
forming a self-assembled monolayer enriched with the low-carbon precursor molecules as the precursor layer.

8. The method as claimed in claim 1, comprising:
pretreating the substrate thereby generating a hydrophobic surface of the substrate, the hydrophobic surface exposed to water vapor in an exposure step thereby generating a surface statistically enriched with OH groups, wherein depositing further comprises:
depositing the low-carbon precursor molecules on the enriched surface thereby subsequently generating a hydrophilic surface having hydrophobic islands of the low-carbon precursor molecules, the high-carbon precursor molecules deposited on the subsequently generated hydrophilic surface thereby forming the precursor layer.

9. The method as claimed in claim 1, wherein depositing further comprises:
one or more of depositing the low-carbon precursor molecules at a temperature of 5 to 30 degrees Celsius, and depositing the high-carbon precursor molecules at a temperature of greater than 40 degrees Celsius.

10. The method as claimed in claim 1, in which the high-carbon precursor molecules are deposited in the deposition step after deposition of the low-carbon precursor molecules after expiration of a crosslinking time, during which the deposited low-carbon precursor molecules are crosslinked with one or more of one another and the substrate at a crosslinking temperature.

11. The method as claimed in claim 1, wherein depositing further comprises:
depositing one or more of the high-carbon precursor molecules and the low-carbon precursor molecules by one or more of atomic layer deposition, vapor deposition, and liquid-phase deposition.

12. The method as claimed in claim 1, wherein depositing further comprises:
one or more of hydrophobically terminating low-carbon precursor molecules with at least one nitrogen group, and depositing at least one amide group.

* * * * *